(12) United States Patent
Korsgren et al.

(10) Patent No.: US 7,981,873 B1
(45) Date of Patent: Jul. 19, 2011

(54) USE WITHIN TRANSPLANTATION SURGERY

(75) Inventors: Olle Korsgren, Uppsala (SE); William Bennet, Stockholm (SE); Bo Nilsson, Uppsala (SE); Rolf Larsson, Uppsala (SE)

(73) Assignee: Corline Systems AB, Uppsala (SE)

( * ) Notice: Subject to any disclaimer, the term of this patent is extended or adjusted under 35 U.S.C. 154(b) by 888 days.

(21) Appl. No.: 09/890,936

(22) PCT Filed: Feb. 4, 2000

(86) PCT No.: PCT/SE00/00223
§ 371 (c)(1),
(2), (4) Date: Nov. 7, 2001

(87) PCT Pub. No.: WO00/45837
PCT Pub. Date: Aug. 10, 2000

(51) Int. Cl.
*A61K 31/727* (2006.01)
(52) U.S. Cl. .......................... 514/56; 424/93.7
(58) Field of Classification Search ............... 514/10, 514/56; 424/93.7
See application file for complete search history.

(56) References Cited

U.S. PATENT DOCUMENTS

| | | | |
|---|---|---|---|
| 5,635,178 A | | 6/1997 | Sims et al. |
| 5,705,270 A | * | 1/1998 | Soon-Shiong et al. ..... 428/402.2 |

FOREIGN PATENT DOCUMENTS

| | | | |
|---|---|---|---|
| DE | 196 23 440 | * | 12/1997 |
| DE | 19623440 A1 | * | 12/1997 |
| JP | 06-510783 A | | 12/1994 |
| JP | 10-291939 A | | 11/1998 |
| JP | 2001-523094 A | | 11/2001 |
| WO | WO 91/05855 | | 5/1991 |
| WO | 93/05793 A1 | | 4/1993 |
| WO | WO 93/05793 | | 4/1993 |
| WO | 93/23085 A1 | | 11/1993 |
| WO | WO 97/11607 | | 4/1997 |
| WO | 98/42850 A1 | | 10/1998 |

OTHER PUBLICATIONS

Lenchow et al., Long-Term Survival of Xenogeneic Pancreatic Islet Grafts Induced by CTLA4Ig, Aug. 7, 1992, Science, vol. 257 pp. 789-792.*
Diabetes Dateline, http://diabetes.niddk.nih.gov/about/dateline/wint00/1.htm Winter 1999-2000.*
Preliminary Results of ITN Multicenter Islet Transplant Trial Confirm Potential Patient Benefits, Underscore Steep Learning Curve, http://drinet.org/html/june_2_2003.htm Jun. 2, 2003.*
Islet Transplant Info http://www.afdr.ab.ca/transplant.html.*
Bennet et al. (Incompatibility Between Human Blood and Isolated Islets of Langerhans: A Finding With Implications for Clinical Intraportal Islet Transplantation, Diabetes, 1999 vol. 48 pp. 1907-1914.*
Couser et al. The Effects of Soluble Recombinant Complement Receptor 1 on Complement-Mediated Experimental glomerulonephritis, Journal of the American Society of Nephrology 1995 vol. 5 No. 11 pp. 1888-1894.*
Hill, et al. *Immunoisolation of Adult Porcine Islets for the Treatment of Diabetes Mellitus, Annals of the New York Academy of Sciences*, vol. 831, (Dec. 31, 1997), pp. 332-343.
Hopt, et al. *Prevention of Early Postoperative Graft Thrombosis in Pancreatic Transplantation, Transplantation Proceedings*, vol. 25, No. 4 (Aug. 1993), pp. 2807-2608.
Nomura, et al. *Unpurified Islet Cell Transplantation in Diabetic Rats, Transplantation Proceedings*, vol. 28, No. 3 (Jun. 1996), pp. 1849-1850.
Rigotti, et al. *Use of Defibrotide in Preventing Vascular Thrombosis in Experimental Pancreas Transplantation*, Dialog Information Services, File 73, EMBASE, Dialog Ascession No. 04002091, Embase Accession No. 1989171087, (1989).
Sefton, et al. *Making Microencapsulation Work: Conformal Coating Immobilization Gels and in vivo Performance, Journal of Controlled Release*, vol. 62 (2000), pp. 173-186.
Tatarkiewicz, et al. *In vitro and in vivo Evaluation of Protamine-Heparin Membrane for Microencapsulation of Rat Langerhans Islets.*, Dialog Information Services, File 155, Medline, Dialog Accession No. 08102103, Medline Accession No. 95134104, (1994).
Tollemar, et al. *Anticoagulation Therapy for Prevention of Pancreatic Graft Thrombosis: Benefits and Risks, Transplantation Proceedings*, vol. 20, No. 3 (Jun. 1988), pp. 479-480.
English translation of Office Action in corresponding Japanese Application No. 2000-596956.
Normura, et al "Unpurified Islet Cell Transplantation in Diabetic Rats" Transplantation Proceedings, 28(3): 1849-1850 (1996).
London, et al "Pancreas and islet transplantation" British Journal of Surgery, 79(1): 6-7 (1992).
Rosenfeld, et al "Human Platelet Receptor for Immunoglobulin G" J. Clin. Invest., 76: 2317-2322 (1985).

* cited by examiner

*Primary Examiner* — James D Anderson
(74) *Attorney, Agent, or Firm* — Browdy and Neimark, PLLC

(57) ABSTRACT

The present invention is within the field of transplantation surgery. More closely, the present invention relates to use of a clotting preventing agent in the production of a drug for administration in association with transplantation of insulin producing cells in the form of isolated islets to patients with insulin dependent diabetes mellitus, IDDM. The invention is expected to significantly improve the clinical outcome of transplantation of islets of Langerhans.

Figure 1:
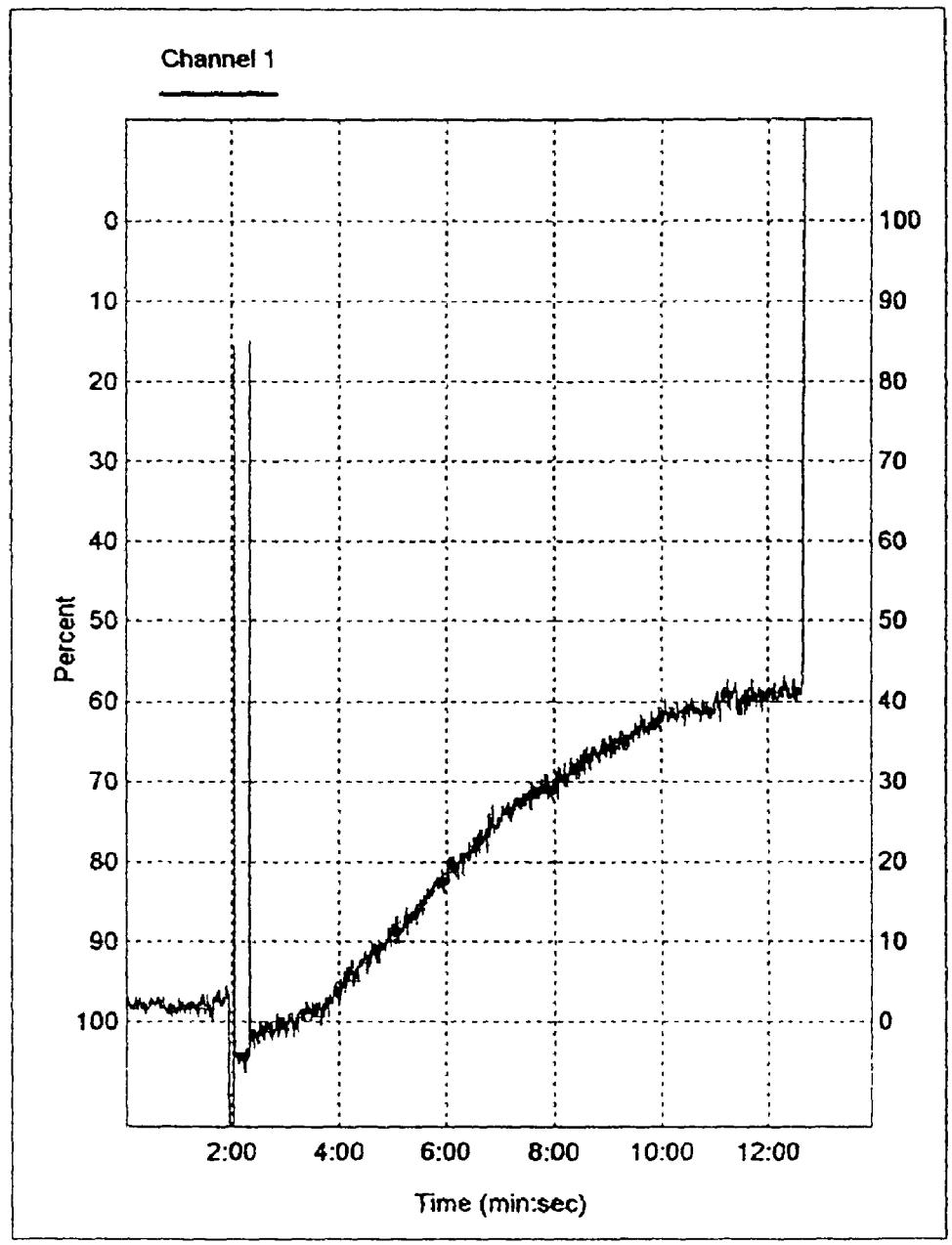

7 Claims, 3 Drawing Sheets

USE WITHIN TRANSPLANTATION SURGERY

REFERENCE TO RELATED APPLICATIONS

The present application is the national stage under 35 U.S.C. 371 of international application PCT/SE00/00223, filed Feb. 4, 2000 which designated the United States, and which international application was published under PCT Article 21(2) in the English language.

FIELD OF THE INVENTION

The present invention is within the field of transplantation surgery. More closely, the present invention relates to use of a clotting preventing agent in the production of a drug for administration in association with transplantation of cells and tissue, such as insulin producing cells to patients with insulin dependent diabetes mellitus, IDDM.

BACKGROUND OF THE INVENTION

The only option to achieve permanent normoglycemia in diabetic patients is a renewal of the β-cells, either by transplantation of segmental/whole pancreas or isolated islets of Langerhans. Transplantation of isolated islets is considerably less successful compared to whole pancreas transplantation. The immunological barrier, the underlying autoimmune disease and the immunosuppressive drugs used, are the same in both types of transplantation. Thus, there is no obvious immunological explanation as to why transplantation of whole pancreas is more successful than islet transplantation.

If, however, the problems related to the unsuccessful outcome of transplantation of islets were identified and a technical and practical solution was developed, obvious benefits for the patients would be created implying interesting commercial opportunities.

The prior art in this field is largely confined to measures aiming at reducing immunological reactions. WO 9711607 describes transplantation of microencapsulated insulin producing cells as a means of protecting the cells from immunological reactions and/or combined with treating the recipient with a substance that would inhibit an immune-system costimulation. WO 9105855 describes transplantation of islets of animal origin and that the animal tissue should be modified to contain homologous complement restriction factors. DE 19623 440 A 1 describes methods for encapsulation of islets and points out that the artificial encapsulation material may induce platelet activation, coagulation and complement activation, and therefore the encapsulation material should be modified to allow release of inhibiting substances as e.g., heparin, hirudin or Marcumar. U.S. Pat. No. 5,635,178 is not related to transplantation of islets but describes monoclonal antibodies having inhibitory activity towards the terminal complex of complement and that such antibodies can be used to reduce activation of platelets and endothelial cells.

It is evident for those skilled in the art that measures aiming at inhibiting immunological reactions in connection with transplantation of islets regardless of being allogenic or xenogenic have not lead to a satisfactory result in respect of clinical outcome.

SUMMARY OF THE INVENTION

The present inventors have performed experiments implying adding human, adult porcine or fetal porcine islets to human whole blood and have been struck by the vigorous coagulation occurring when these islets were injected into human ABO-compatible blood. As judged by microscopical examinations it is evident that the islets are rapidly coated by a layer of platelets which soon develops into an organised thrombus. This biological event has previously not been considered and is now suggested to be a major explanation as to why the outcome of autologous islet transplantation has been comparatively unsuccessful. The present invention is related to measures to reduce this incompatibility reaction that can either be directed towards inhibiting activation of platelets, mono- or polymorhonuclear cells or the enzyme cascade of coagulation. Regardless of the initiating event, any of these reactions will lead to generation of thrombin, which eventually converts fibrinogen to fibrin. The generation of thrombin can easily be monitored by measuring the thrombin-antithrombin complex (TAT complex). Hence, the present invention is concerned with therapeutic measures to inhibit TAT complex formation upon exposure of allogenic or xenogenic islets to whole blood.

Therefore, the present invention relates to a use of a clotting preventing agent in the production of a drug for administration in connection with transplantation of cells and tissue, such as insulin producing cells in the form of isolated islets to patients with insulin dependent diabetes mellitus, IDDM.

Preferably, the clotting preventing agent is an anticoagulant, such as heparin or fractions or derivatives thereof. Alternatively, hirudin, oxalate, citrate etc. can be used.

In one embodiment of the invention, the islet cells are coated with heparin or fractions or derivatives thereof by preincubation of islets in a solution containing heparin or fractions or derivatives thereof. Using a conjugate of heparin to coat the islets, it was demonstrated that the modified islets had acquired an increased capacity to adsorb antithrombin and loop experiments (described below) demonstrated that it is possible to reduce clotting by using such modified islets.

In an alternative embodiment of the invention, the preventing agent is an inhibitor of platelet activation, such as a RGD (standard one letter code for amino acids) containing peptide or a monoclonal antibody which inhibits the interaction of platelet integrins with their specific ligands. This antibody is for example a monoclonal antibody or a peptide directed against the Fc receptor on platelets.

A combination of anticoagulant and inhibitor of platelet activation can be used as clotting preventing agent according to the invention or any other suitable combination of preventing agents. Optionally, the preventing agent(s) is/are supplemented by an inhibitor of complement.

Furthermore, the invention relates to a method for increasing survival of islet cells in connection with transplantation of insulin producing cells to patients with insulin dependent diabetes mellitus, IDDM, comprising prevention of clotting, monitored as reduced generation of thrombin-antithrombin complex.

DETAILED DESCRIPTION OF THE INVENTION

Figure 2:
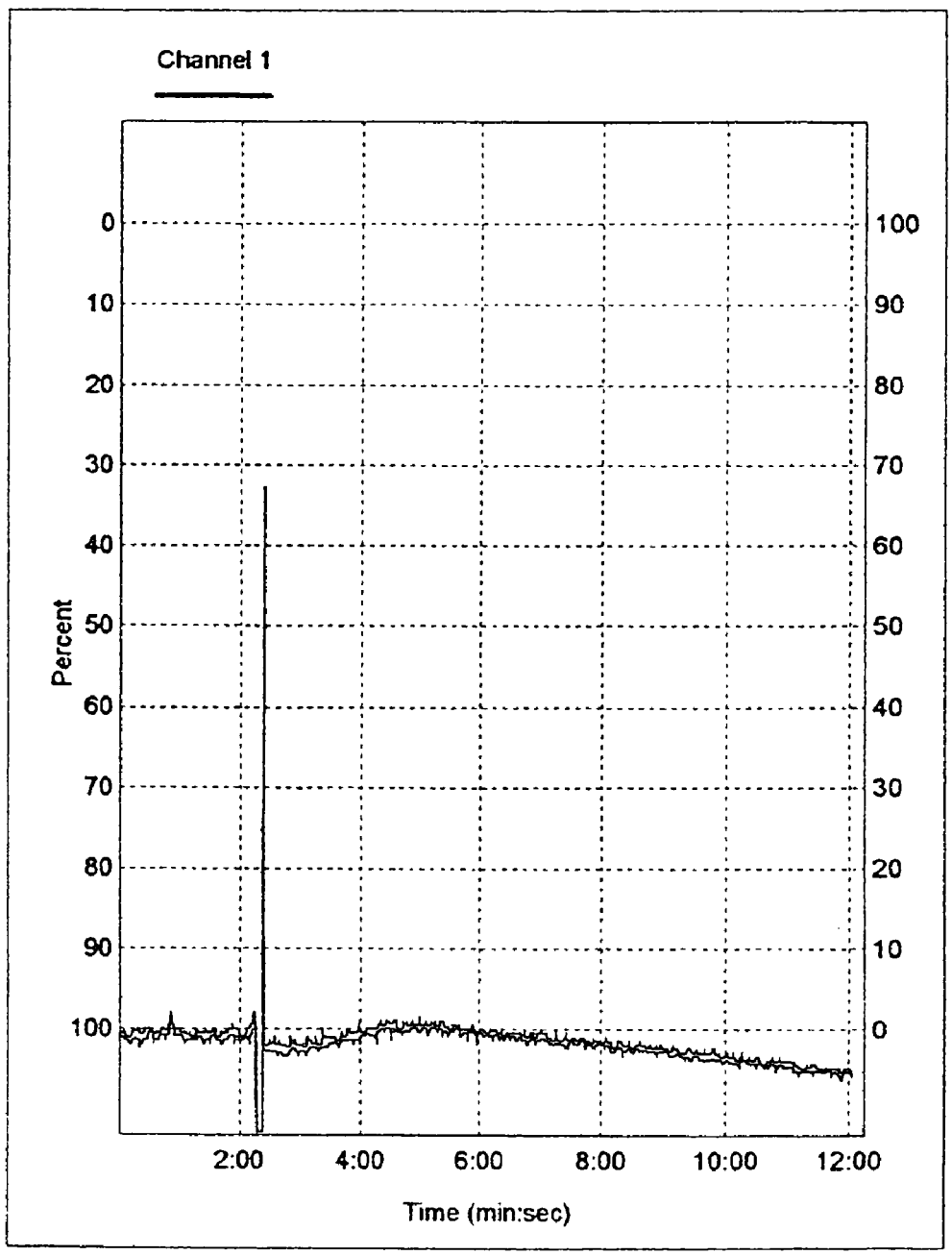
Figure 3:
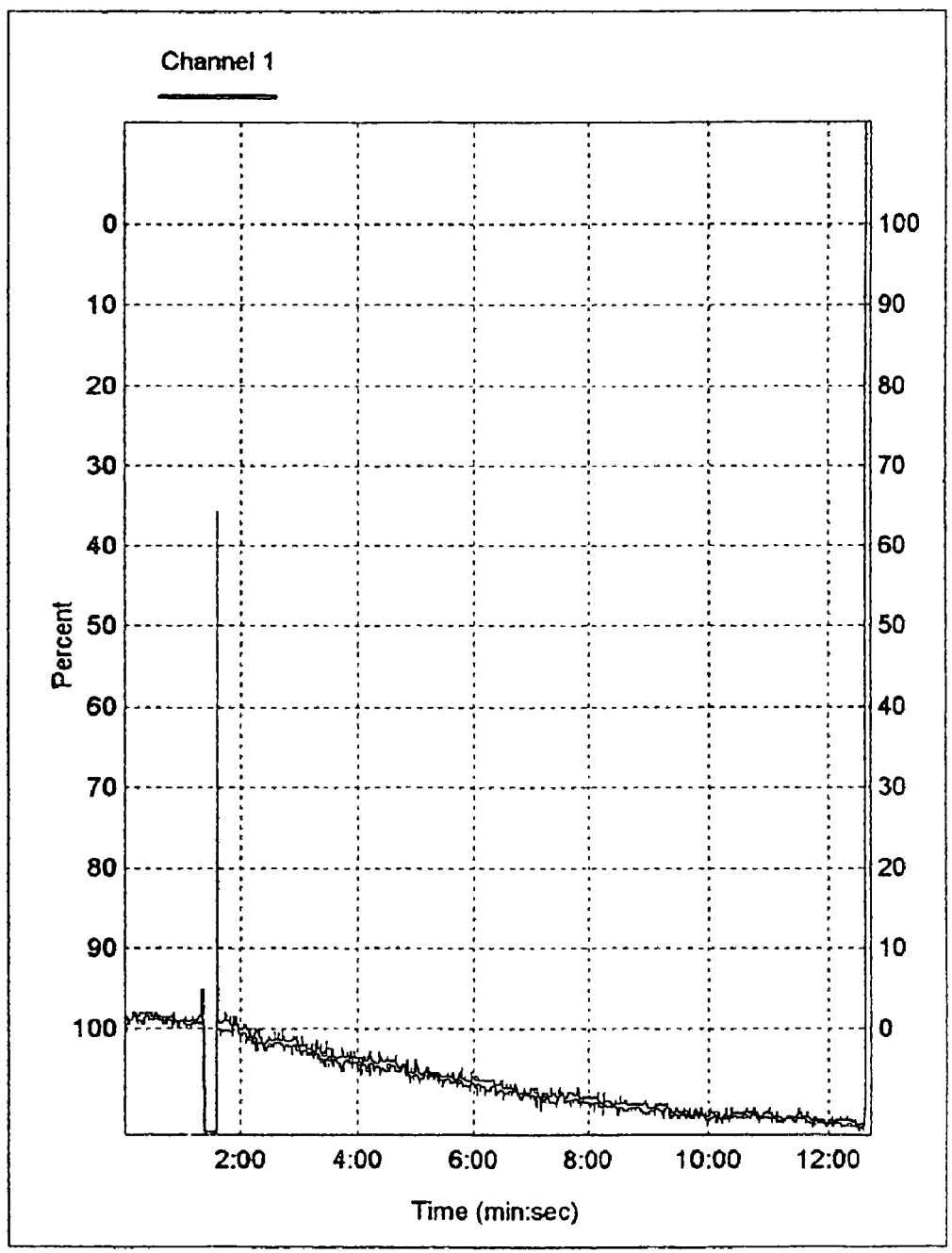

The invention will be described more closely below in association with the accompanying drawings, in which FIG. 1 is a graph showing percent aggregation of platelets following addition of islets to platelet rich plasma, PRP, as a function of time;

FIG. 2 shows a similar graph as in FIG. 1 but here a RGDS (standard one letter code for amino acids; SEQ ID NO:1) tetrapeptide was added to PRP before islets were added; and FIG. 3 shows a similar graph as in FIGS. 1 and 2 but here a monoclonal antibody against the Fc receptor on platelets was added to PRP before islets were added.

All the in vitro experiments for studies of islets contacting whole blood were performed in a tubing loop model. The experimental model is a modification of a model for testing biomaterials that has previously been described (J. Clin. Immunol. 16, 223-230 (1996)). Tubings made of polyvinyl-chloride (PVC, i.d.=6.3 mm, length=300 mm) were modified with immobilized heparin according to a method developed by Corline Systems AB (Uppsala, Sweden) as disclosed in international patent application no WO93/05793. Briefly, the polymer surface is modified with a high molecular weight amine compound to add primary amine groups to the surface. A soluble conjugate prepared by covalent binding of approximately 60 mol of heparin per mol of a straight-chained poly-allylamine is irreversibly bonded onto the amine surface of the tubings. This procedure results in a total surface concentration of heparin of approximately 0.5 µg/cm$^2$. By using such heparin modified tubings it is possible to incubate the tubings with non-anticoagulated fresh human blood in a rocking device at 37° C. for one hour with only moderate activation of blood (c.f. control column in Table 1 A and 1 B below). Unmodified tubings will invariably induce complete clotting at these experimental conditions. Addition of human islets or porcine adult or fetal islets lead to some remarkable observations. Complete clotting invariably occurred with a total loss of platelets, a sharp increase in the formation of TAT and a very significant increase in the markers of the early contact phase (FXIIa and FXIa) of coagulation (C.f. Table 1 A and 1 B). Histological examination revealed a dense layer of activated platelets immediately adjacent to the capsule of the islets.

The findings in vitro described above were confirmed in vivo by evaluation of porcine islets after intraportal transplantation in pigs. The porcine livers, removed 60 min. after islet transplantation, had a congested appearance with patchy dark discoloration's on the surface. In the portal veins blood clots were found, with a patchy adherence to the endothelium, and branching into the portal tree, partially occluding the vessels. The histological examination revealed islets entrapped in blood clots, with a disrupted islet morphology. Occasionally a fibrin tail could be observed extending away from the islet.

With reference to Table 1B, it appears that the effect of adding an inhibitor of complement leads to reduced activation of complement, as expected, but there is no measurable effect on the clotting of blood or activation of platelets. If, however, soluble heparin was added to the experimental system there was a remarkable improvement in preservation of the number of platelets and reduced generation of TAT.

In another set of experiments the effects of inhibiting the interaction between platelet integrins and their specific ligands were investigated. With reference to FIGS. 1-3, it appears that platelet aggregation is induced upon contact with islets and that such aggregation can be prevented by blocking platelet integrins or Fc-receptors.

Porcine islets were surface modified by incubation in a buffered solution containing a high molecular weight conjugate of heparin (Corline Heparin Conjugate), as disclosed in WO 93/05793, and then rinsed by changing buffer several times. It was demonstrated that the modified islets had acquired an increased capacity to adsorb antithrombin and loop experiments showed that heparin modified islets resulted in reduced clotting compared to unmodified islets.

It is easily understood by those skilled in the art that there is a broad arsenal of agents that can be used to accomplish reduced clotting, and hence, the following non-limiting Examples are only used to demonstrate the principle behind the present invention.

Example 1

Effect of Soluble Heparin

Sixty ml of non-anticoagulated blood was collected from healthy blood donors using heparin-coated equipment. U-shaped tubings with a total volume of nine ml were filled with eight ml of blood immediately followed by addition of isolated human islets or porcine adult or porcine fetal islets (500 IEQ). The tubings were then closed into loops using connectors of titanium furnished with immobilised heparin. The tubing loops were placed vertically in a rocking device and the complete apparatus was placed in an incubator at 37° C. for up to sixty minutes. At the end of the rocking period blood was collected in EDTA and the number of cells were counted in a automatic cell counter. The blood samples were then centrifuged at 4° C. (3290×g, 20 min) and EDTA plasma was collected and immediately put at −70° C. Islets retrieved after blood perifusion were prepared for immunohistochemistry. The results are summarized in Table 1A and 1B below.

Table I A shows results of blood cell counts and coagulation and complement parameters before and after 60 min. of human islet perifusion with ABO-compatible fresh human blood or blood supplemented with heparin.

TABLE 1A

Blood cell counts and coagulation and complement parameters before and after 60 min. of human islet perifusion with ABO-compatible fresh human blood or blood supplemented with heparin.

| | | | HUMAN ISLETS | |
|---|---|---|---|---|
| | BEFORE | CONTROL | WITHOUT ADDITIVES | HEPARIN |
| Platelets (×10$^9$) | 233 ± 13.8 | 161.1 ± 9.3 | 5 ± 0.3*** | 114 ± 17* |
| Neutra. (×10$^9$) | 3.23 ± 0.33 | 3.03 ± 0.32 | 0.83 ± 0.18*** | 2.56 ± 0.43 |
| Mono. (×10$^9$) | 0.36 ± 0.03 | 0.36 ± 0.04 | 0.03 ± 0.01*** | 0.28 ± 0.06 |
| Lymph. (×10$^9$) | 1.91 ± 0.12 | 1.77 ± 0.12 | 1.29 ± 0.12** | 1.60 ± 0.20 |
| C3$_a$ (ng/mL) | 84 ± 4.7 | 507 ± 115 | 1259 ± 125.1*** | 565 ± 143.6 |
| C5b-9 (AU/mL) | 15.6 ± 2.9 | 95 ± 30 | 213 ± 43.4* | 147 ± 39.6 |
| FXIIa-AT (umol/L) | 0.09 ± 0.01 | 0.36 ± 0.15 | 12.9 ± 0.9*** | 5.4 ± 1.7** |
| FXIa-AT (umol/L) | 0.06 ± 0.01 | 0.12 ± 0.03 | 4.74 ± 0.48*** | 0.34 ± 0.12* |
| TAT (ug/mL,) | 12.5 ± 5.2 | 316 ± 100 | 20537 ± 1973*** | 4467 ± 2285 |

Control loops contained blood and culture medium (RPMI), but no islets. All values are stated as the Mean ± SE(M).
TAT, Thrombin-antithrombin. The degree of significance is reported with respect to the controls.
(*p < 0.05; p < 0.01; *p < 0.001; n.a. = not analysed).

Table I B shows results of blood cell counts and coagulation and complement parameters before and after 60 min. of adult and fetal porcine islet perifusion with fresh human blood or blood supplemented with the complement inhibitor C1 inactivator (C1-INA) or heparin.

when islets were added to PRP (FIG. 2). A similar finding was obtained if the anti-Fc receptor antibody was added (FIG. 3).

Conclusion: The experiments show that islets bind to platelets when added to PRP. This binding induce activation and aggregation of the platelets.

TABLE 1B

Blood cell counts and coagulation and complement parameters before and after 60 min. of adult and fetal porcine islet perifusion with fresh human blood or blood supplemented with C1-INA or heparin.

| | | | ADULT ISLETS | | | FETAL ISLETS |
|---|---|---|---|---|---|---|
| | BEFORE | CONTROL | WITHOUT ADDITIVE | C1-INA | HEPARIN | WITHOUT ADDITIVES |
| Platelets ($\times 10^9$) | 237 ± 8.0 | 171 ± 9.0 | 4 ± 0.1*** | 4 ± 0 | 145 ± 13.0 | 4 ± 0*** |
| Neutrophils ($\times 10^9$) | 2.75 ± 0.21 | 2.52 ± 0.21 | 0.57 ± 0.07*** | 0.41 ± 0.13 | 3.00 ± 0.19 | 1.44 ± 0.17** |
| Monocytes ($\times 10^9$) | 0.38 ± 0.02 | 0.37 ± 0.02 | 0.04 ± 0.01*** | 0.15 ± 0.01 | 0.35 ± 0.05 | 0.07 ± 0.01*** |
| Lymphcytes ($\times 10^9$) | 2.30 ± 0.14 | 2.13 ± 0.11 | 1.74 ± 0.10* | 1.23 ± 0.38 | 1.88 ± 0.11 | 1.68 ± 0.25 |
| C3a (ng/mL) | 80.1 ± 7.3 | 545 ± 68 | 1435 ± 173*** | 1094 ± 78 | 486 ± 139 | 1601 ± 215*** |
| C5b-9 (AU/mL) | 15.8 ± 1.8 | 72 ± 10 | 283 ± 34*** | 183 ± 29 | 82 ± 22 | 302 ± 46*** |
| FNIIa-AT (mmol/L) | 0.18 ± 0.03 | 0.13 ± 0.00 | 8.96 ± 1.38*** | 19.65 ± 0.45 | 3.56 ± 1.60** | n.a. |
| FXIa-AT (mmol/L) | 0.04 ± 0.00 | 0.03 ± 0.00 | 4.14 ± 0.48*** | 2.95 ± 0.15 | 0.53 ± 0.26 | n.a. |
| TAT (ug/mL) | 5.6 ± 1.1 | 139 ± 35 | 23886 ± 3494*** | 30250 ± 3450 | 505 ± 162*** | 34420 ± 4875 |

Control loops contained blood and culture medium (RPMI), but no islets. All values are stated as the Mean SE(M). TAT, Thrombin-antithrombin. The degree of significance is reported with respect to the controls.
(*p<0.05; 0.01; *p<0.001; n.a.. = not analysed).

C1 inactivator reduced complement activation but had no detectable effect on the coagulation parameters. Soluble heparin, however, prevented clotting and there was a remarkable improvement with respect to platelet count and generation of TAT. Notwithstanding the results obtained by the use of C1-INA, it is obvious that it should be beneficial to combine an anticoagulant with an inhibitor of complement.

Example 2

Effect of Platelet Inhibitor

Platelets in platelet rich plasma (PRP) and gel filtered platelets were tested in an aggregometer. Islets were added to PRP and thereafter analysed in the aggregometer. It was shown that the islets induced aggregation of the platelets (FIG. 1) and that platelets number in the sample were reduced from $375\times 10^9$ to $236\times 10^9$. If purified platelets without plasma proteins were used in combination with islets no aggregation and reduction in the platelet count were observed. In attempts to identify the mechanism behind the induced aggregation, an RGDS tetrapeptide to inhibit integrin binding and a monoclonal antibody against Fc receptors on platelets were used. Addition of the RGDS peptide totally abolished the aggregation and the consumption of platelets Example 3

Effect of Surface Modification of Islets Using a Heparin Conjugate

Using Corline Heparin Conjugate (c.f. WO 93/05793) containing approximately sixty mol of heparin covalently bound to one mol of straight-chained carrier, adult porcine islets were modified by irreversible adsorption of the heparin conjugate onto the surface of the islets. This was accomplished by incubating the islets for 30 minutes at 37° C. in a buffered saline solution containing heparin conjugate.

The presence of heparin at the surfaces of the islets was demonstrated by an ELISA assay for islet surface associated antithrombin (AT). Unmodified and heparin modified islets were incubated in human plasma for thirty minutes and then rinsed several times by changing buffer. The islet were then incubated with anti-AT that had been labelled with biotin. Using HRP-labelled streptavidin the uptake of anti-AT could be semiquantitatively estimated. The uptake of anti-AT on the heparin modified islets was three times higher than that on the unmodified islets showing that biologically active heparin was present on the surface of the islets. Testing of heparin modified islets in the tubing loop model resulted in less clotting compared to unmodified islets.

The present invention is expected to significantly improve the situation for IDDM patients. By administering an anticoagulant and/or inhibitor of platelet activation, optionally in combination with surface modification of islets, and optionally together with a complement inhibitor, in association with transplantation of insulin producing cells it is expected that the need of providing these patients with injections of insulin will be substantially decreased or even eliminated.

The invention claimed is:

1. A method comprising
transplantation of insulin producing cells in the form of individually isolated islets to a patient suffering from insulin dependent diabetes mellitus (IDDM),
wherein said individually isolated islets are modified by irreversible adsorption with a clotting inhibiting agent comprising heparin or a conjugate thereof onto the surfaces of the islets,
wherein said individual islet cells are each separately coated with heparin or a conjugate thereof by preincubation of the islets in an aqueous solution containing heparin or a conjugate thereof,
wherein said clotting inhibiting agent acts to inhibit clotting or reduce clotting.

2. The method according to claim 1, wherein more than one clotting inhibiting agent is used.

3. The method according to claim 1, wherein the clotting inhibiting agent is supplemented by an inhibitor of complement.

4. Isolated islets comprising insulin producing cells, wherein the islets are individually coated with heparin or a conjugate thereof on the islet surface.

5. A method for increasing survival of islet cells according to claim 4, in connection with transplantation of insulin producing cells to patients with insulin dependent diabetes mellitus (IDDM), comprising inhibiting of clotting, monitored as reduced generation of thrombin-antithrombin complex (TAT complex).

6. A method of using the isolated islets of claim 4, comprising
injecting said islets individually coated with heparin or a conjugate thereof into the bloodstream of a patient suffering from insulin dependent diabetes mellitus (IDDM).

7. A method comprising transplantation of insulin producing cells in the form of isolated islets to a patient suffering from insulin dependent diabetes mellitus (IDDM),
wherein said isolated islets are modified by irreversible adsorption of a clotting inhibiting agent comprising heparin or a conjugate thereof onto the surface of the islets;
said modification comprising incubating said islets in a solution of heparin or a conjugate thereof;
wherein said clotting inhibiting agent acts to inhibit or reduce clotting.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: synthetic

<400> SEQUENCE: 1

Arg Gly Asp Ser
1
```